US008675814B2

(12) United States Patent
Akahori et al.

(10) Patent No.: US 8,675,814 B2
(45) Date of Patent: Mar. 18, 2014

(54) RADIOGRAPHY APPARATUS INCLUDING A BODY THICKNESS INFORMATION OBTAINMENT UNIT

(75) Inventors: Sadato Akahori, Kanagawa-ken (JP); Jun Enomoto, Kanagawa-ken (JP); Eiichi Kanagawa, Kanagawa-ken (JP); Yasunori Ohta, Kanagawa-ken (JP); Noriaki Ida, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 521 days.

(21) Appl. No.: 12/923,557

(22) Filed: Sep. 28, 2010

(65) Prior Publication Data
US 2011/0075793 A1    Mar. 31, 2011

(30) Foreign Application Priority Data

Sep. 28, 2009 (JP) ................................. 2009-222252
Aug. 31, 2010 (JP) ................................. 2010-193198

(51) Int. Cl.
*A61B 6/02* (2006.01)
*H05G 1/60* (2006.01)
*H05G 1/64* (2006.01)

(52) U.S. Cl.
USPC ................... 378/26; 378/22; 378/25; 378/95; 378/196; 378/197

(58) Field of Classification Search
USPC ........................... 378/21–27, 37, 196, 197, 95
See application file for complete search history.

(56) References Cited

U.S. PATENT DOCUMENTS

| | | | |
|---|---|---|---|
| 5,526,394 A * | 6/1996 | Siczek et al. ..................... | 378/37 |
| 5,949,811 A * | 9/1999 | Baba et al. ..................... | 378/108 |
| 6,377,656 B1 * | 4/2002 | Ueki et al. ..................... | 378/98.7 |
| 6,415,015 B2 * | 7/2002 | Nicolas et al. ................. | 378/62 |
| 6,426,996 B1 * | 7/2002 | Moribe et al. ................. | 378/116 |
| 6,751,285 B2 * | 6/2004 | Eberhard et al. ............... | 378/37 |
| 6,795,526 B2 * | 9/2004 | Kump et al. ................... | 378/116 |
| 6,827,489 B2 * | 12/2004 | Nicolas et al. ................ | 378/205 |
| 6,914,958 B2 * | 7/2005 | Ganin ............................ | 378/26 |
| 6,934,362 B2 * | 8/2005 | Scheuering ................... | 378/108 |
| 6,942,385 B2 * | 9/2005 | Fadler et al. .................. | 378/205 |
| 6,970,531 B2 * | 11/2005 | Eberhard et al. .............. | 378/26 |
| 6,973,160 B2 * | 12/2005 | Matsumoto ................... | 378/22 |
| 6,980,624 B2 * | 12/2005 | Li et al. ......................... | 378/23 |
| 7,123,683 B2 * | 10/2006 | Tsujii ............................ | 378/26 |
| 7,123,684 B2 * | 10/2006 | Jing et al. ...................... | 378/37 |
| 7,245,694 B2 * | 7/2007 | Jing et al. ...................... | 378/37 |
| 7,292,675 B1 | 11/2007 | Li et al. | |

(Continued)

FOREIGN PATENT DOCUMENTS

JP    2003-299643    10/2003
JP    2005-149762    6/2005

*Primary Examiner* — Allen C. Ho
(74) *Attorney, Agent, or Firm* — Jean C. Edwards, Esq.; Edwards Neils PLLC

(57) ABSTRACT

When a subject is irradiated with radiation, and the radiation that has passed through the subject is detected, body thickness information about the subject is obtained. Further, a slice image obtainment condition representing a range in which a slice image is obtained in the subject is set based on the body thickness information. Further, the slice image is obtained based on the slice image obtainment condition.

4 Claims, 11 Drawing Sheets

(56) References Cited

U.S. PATENT DOCUMENTS

| | | | |
|---|---|---|---|
| 7,302,031 B2 * | 11/2007 | Hjarn et al. | 378/37 |
| 7,313,225 B2 * | 12/2007 | Mertelmeier | 378/116 |
| 7,372,943 B2 * | 5/2008 | Bernhardt | 378/98.12 |
| 7,453,979 B2 * | 11/2008 | Sendai | 378/23 |
| 7,515,682 B2 * | 4/2009 | Li et al. | 378/22 |
| 7,519,155 B2 * | 4/2009 | Mollus et al. | 378/108 |
| 7,545,907 B2 * | 6/2009 | Stewart et al. | 378/37 |
| 7,620,142 B1 * | 11/2009 | Toth | 378/16 |
| 7,697,661 B2 * | 4/2010 | Souchay et al. | 378/37 |
| 7,778,388 B2 * | 8/2010 | Sendai | 378/22 |
| 7,869,563 B2 * | 1/2011 | Defreitas et al. | 378/37 |

* cited by examiner

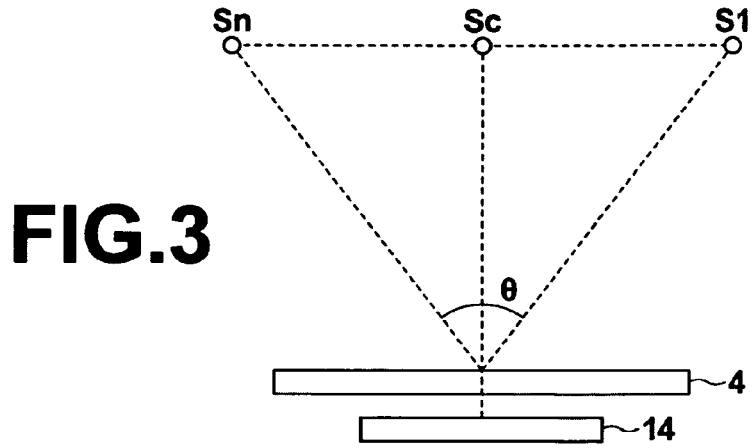
FIG. 3
FIG. 4
| BODY THICKNESS | CENTER PLANE (cm) | PLANE CONSTRUCTION RANGE (cm) |
|---|---|---|
| THICK | 15 | 20 |
| STANDARD | 10 | 10 |
| THIN | 5 | 5 |
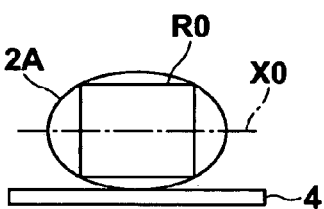 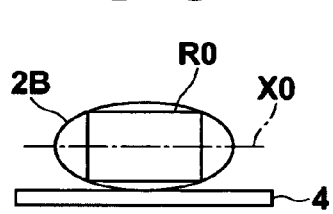 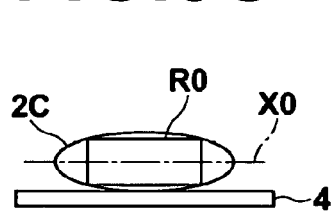
FIG. 5A  FIG. 5B  FIG. 5C
FIG. 6
| BODY THICKNESS | CENTER PLANE (cm) | PLANE CONSTRUCTION RANGE (cm) |
|---|---|---|
| THICK | +3 | +6 |
| STANDARD | 0 | 0 |
| THIN | −3 | −6 |

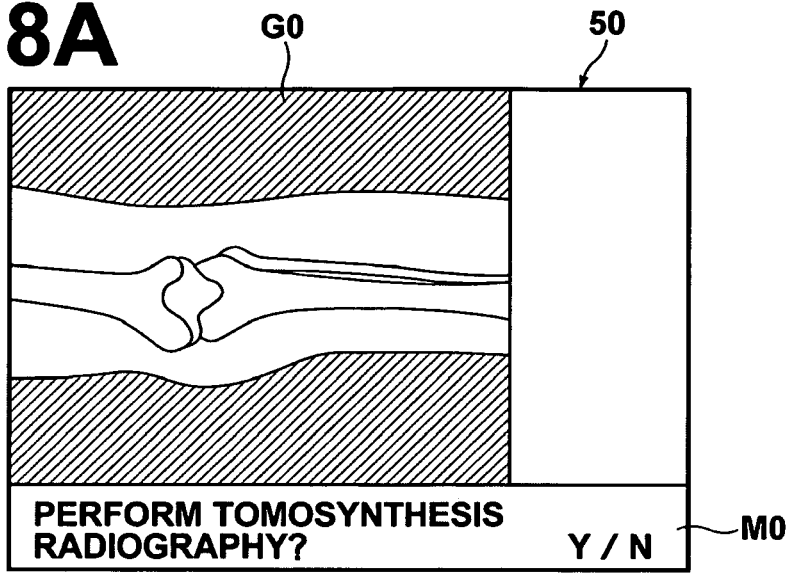
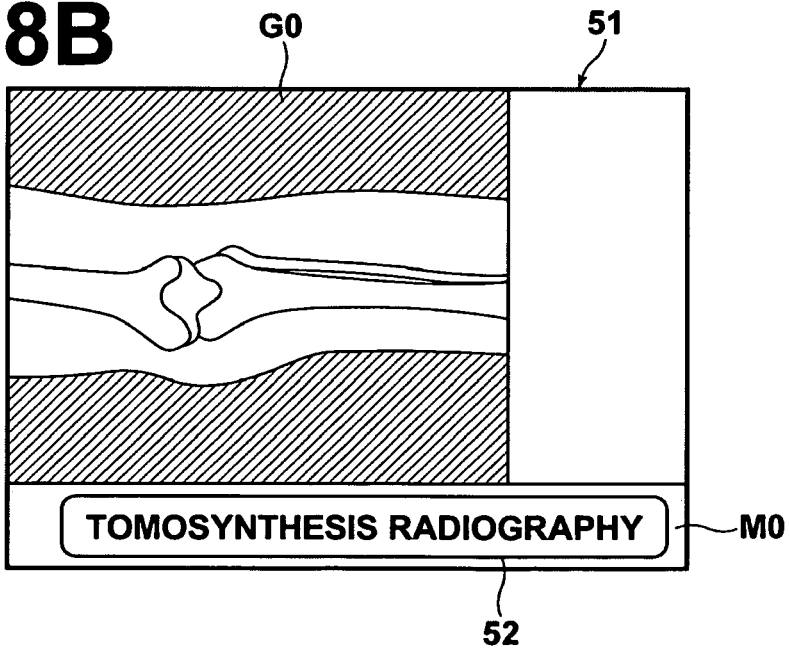

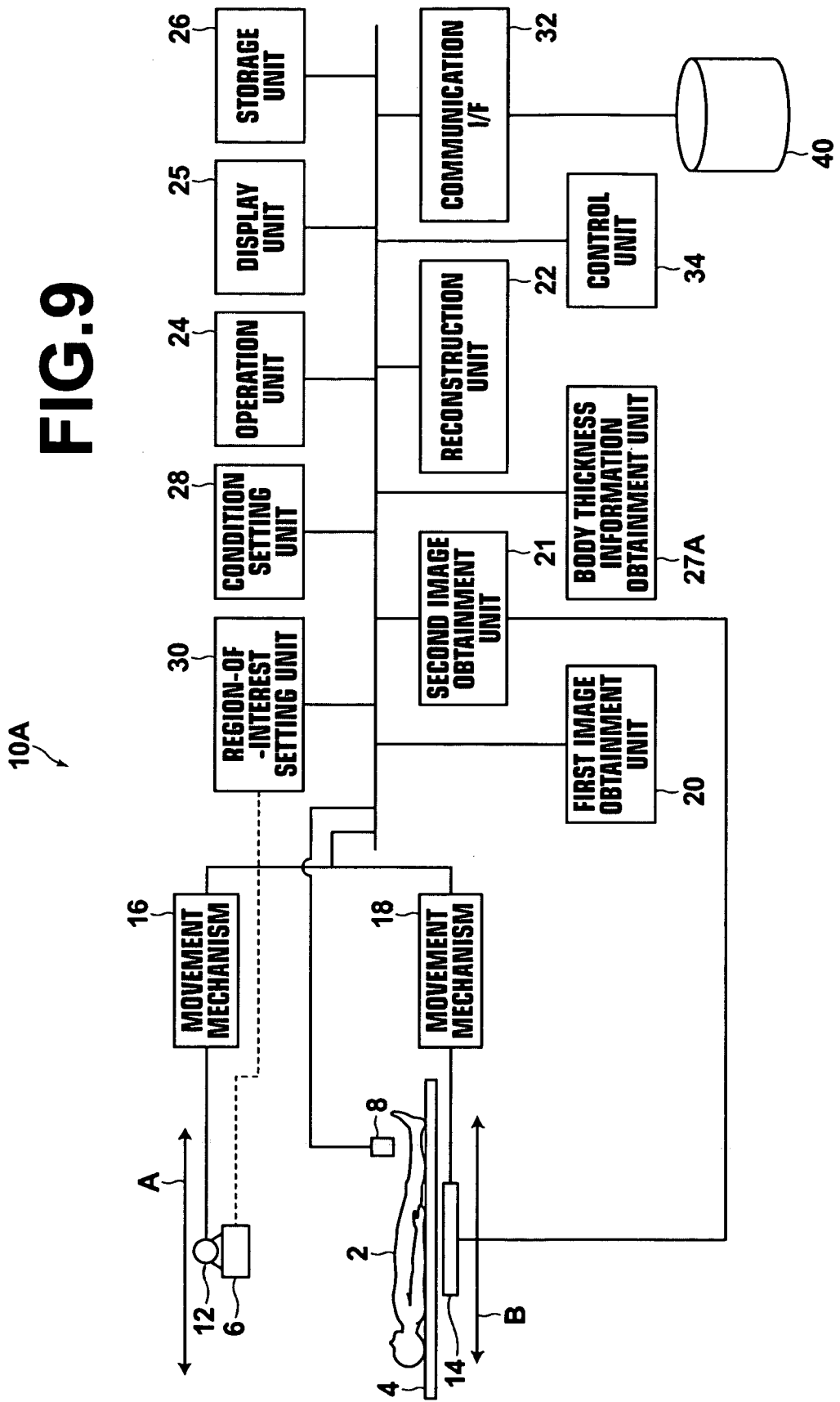

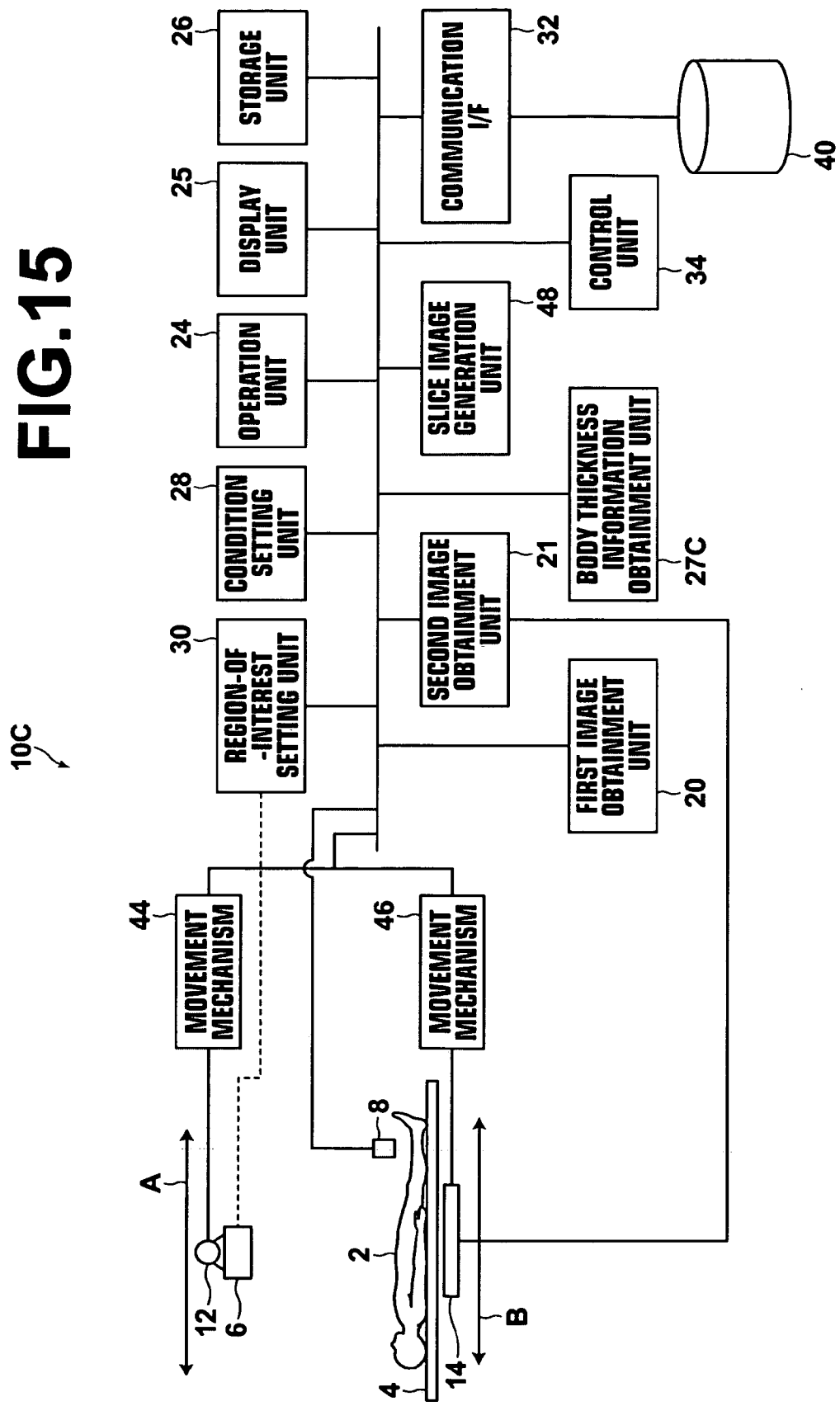

RADIOGRAPHY APPARATUS INCLUDING A BODY THICKNESS INFORMATION OBTAINMENT UNIT

CROSS-REFERENCE TO RELATED APPLICATIONS

The present application claims priority from Japanese Patent Application Nos. 2009-222252, filed Sep. 28, 2009 and 2010-193198, filed Aug. 31, 2010, the contents of all of which are herein incorporated by reference in their entirety.

BACKGROUND OF THE INVENTION

1. Field of the Invention

The present invention relates to a radiography apparatus for performing radiography to generate slice images of a subject.

2. Description of the Related Art

In recent years, tomosynthesis radiography was proposed to observe affected regions of patients in more detail by a radiography apparatus using X-rays. In tomosynthesis radiography, radiography is performed by moving an X-ray tube to different positions, and by irradiating a subject by the X-ray tube at different angles from the different positions. Further, images obtained by radiography are added to obtain an image in which a desired cross section of the subject is emphasized. In tomosynthesis radiography, the X-ray tube is moved parallel to an X-ray detector, or in such a manner to draw a circle or an ellipse or oval, based on the characteristic of a radiography apparatus and the kind of slice images (tomograms) to be obtained. The subject is radiographed at different radiation angles to obtain a plurality of radiographic images, and a slice image of the subject is reconstructed from the plurality of radiographic images. In generation of slice images by tomosynthesis radiography as described above, a slice image of the subject in which a structure on a desired cross-section of the subject is emphasized can be obtained by blurring and suppressing structures which are not on the desired cross-section. Therefore, it is possible to improve the visual recognition characteristic of images in observation of lung nodules or nodes, in which structures overlap with each other and are hard to observe, microfractures of bones, and the like.

Further, in application of tomosynthesis radiography, a method in which pre-shot radiography is performed before tomosynthesis radiography has been proposed (please refer to U.S. Pat. No. 7,292,675 (Patent Document 1)). In the pre-shot radiography, a subject is irradiated with low-dose X-rays. Further, the dose of X-rays in the tomosynthesis radiography is set by using a pre-shot image obtained in pre-shot radiography and the condition of radiography in the pre-shot radiography. Further, a method in which transmission data about a subject is obtained before tomosynthesis radiography has been proposed (please refer to Japanese Unexamined Patent Publication No. 2005-149762 (Patent Document 2)). In the method, the transmittance of the subject is measured based on the transmission data, and the tube voltage of the X-ray tube during radiography is set based on the transmittance. Further, a method in which a region for setting a region of interest is determined based on a past radiographic image of a sample (subject) has been proposed (please refer to PCT Japanese Publication No. 2003-299643 (Patent Document 3)). In the method, the region for setting the region of interest is correlated with scanograms for determining an actually imaged cross-section, and the region of interest, which is an actual range of radiography, is determined. Accordingly, the dose of radiation that passes the outside of the actual region of interest during radiography is limited.

However, Patent Document 1 merely discloses setting the dose of X-rays in tomosynthesis radiography by using a pre-shot image. Further, Patent Document 2 merely discloses setting the tube voltage of an X-ray tube. Further, in the method disclosed in Patent Document 3, it is necessary to refer to a past radiographic image of the subject, obtained in the past radiography, to set a region of interest.

Further, in the method disclosed in Patent Document 2, it is necessary to obtain transmission data to measure the transmittance of the subject before tomosynthesis radiography. Therefore, additional irradiation of the subject with radiation is necessary. Further, in the method disclosed in Patent Document 3, it is necessary to obtain scanograms to set the region of interest. Therefore, additional irradiation of the subject with radiation is required.

When a slice image is generated in a tomosynthesis apparatus, it is necessary to irradiate a subject with X-rays a plurality of times. Therefore, the dose of radiation irradiating the subject is larger than the dose of radiation irradiating the subject in plain radiography (simple radiography), in which an X-ray image of the subject is obtained by irradiating the subject with X-rays only once. Therefore, a plain radiographic image obtained by plain radiography may be used first to diagnose a patient, and a slice image may be generated only when it is necessary. For example, only when a suspected bone fracture cannot be confirmed by using a plain radiographic image, a slice image may be generated.

SUMMARY OF THE INVENTION

In view of the foregoing circumstances, it is an object of the present invention to make it possible to efficiently set a range in which a slice image is obtained when the slice image is obtained.

Further, it is another object of the present invention to prevent the dose of radiation irradiating a subject from increasing when the range in which the slice image is obtained is set.

A radiography apparatus according to the present invention is a radiography apparatus comprising:

a radiation source that outputs radiation to a subject;

a detection means that detects the radiation that has passed through the subject;

a body thickness information obtainment means that obtains body thickness information about the subject;

a condition setting means that sets, based on the body thickness information, a slice image obtainment condition representing a range in which a slice image is obtained in the subject; and a slice image obtainment means that obtains, based on the slice image obtainment condition, the slice image.

As the "range in which a slice image is obtained", one of a reconstruction range of slice images (a range in which slice images are reconstructed) in the depth direction of the subject (a direction in which radiation propagates in such a manner to perpendicularly enter a detector), the position of the center plane of slice planes to be represented by the slice images in the reconstruction range, the range of irradiation with radiation in a plane perpendicular to the depth direction, and the like may be used. Further, a three-dimensional region defined by the reconstruction range and the range of irradiation with radiation is the region of interest. The term "region of interest" refers to a region in which the degree of interest is particularly high in diagnosis using images. In other words, the region of interest is a target for obtaining slice images in the subject.

The "reconstruction range" may be set based on at least one of the position of the center plane of slice planes, the position of the highest plane of the slice planes, and the position of the lowest plane of the slice planes.

The radiography apparatus of the present invention may further include an image obtainment means that obtains a pre-shot image by performing pre-shot radiography in which the radiation is output from the radiation source to the subject. Further, the body thickness information obtainment means may obtain the body thickness information about the subject based on a radiography condition in the pre-shot radiography.

The term "pre-shot radiography" refers to radiography to be performed before radiography for obtaining a slice image is performed. Specifically, the pre-shot radiography may be radiography that is necessary to determine a radiography condition in radiography for obtaining a slice image. Further, the pre-shot radiography may be so-called plain radiography, in which diagnosis is possible by using only an image obtained in one radiography operation.

The term "radiography condition" refers to various conditions used to set the target of radiography. The radiography condition includes not only a condition that is set before pre-shot radiography but also a condition that is obtained in actual radiography. Examples of the condition that is set before radiography are tube voltage of radiation, the dose of irradiation, and the like. These conditions are used to set radiography conditions, such as tube voltage and the dose of radiation, in radiography for obtaining a slice image. Examples of the condition that is obtained in actual radiography are the distribution range of pixel values in a pre-shot image, an exposure amount of a directly-irradiated portion in a pre-shot image, which is obtained by a detection means (detector) by detecting radiation that has not passed through the subject, an exposure time period when automatic exposure control is performed, and the like.

In the radiography apparatus of the present invention, the radiography condition in the pre-shot radiography may be the dose of radiation during the pre-shot radiography or the tube voltage of the radiation source during the pre-shot radiography.

In the radiography apparatus of the present invention, the radiography condition in the pre-shot radiography may be a distribution range of pixel values in the pre-shot image.

The radiography apparatus of the present invention may further include an operation means that makes the slice image obtainment means optionally obtain the slice image after the pre-shot radiography.

In the radiography apparatus of the present invention, the slice image obtainment means may skip, in obtainment of the slice image, radiography by the radiation source located at a position at which the pre-shot radiography was performed, and use the pre-shot image in obtainment of the slice image.

In this case, the radiography apparatus of the present invention may further include a subject-movement detection means that detects the movement of the subject. Further, the slice image obtainment means may perform, in obtainment of the slice image, radiography by the radiation source located at the position at which the pre-shot radiography was performed when the subject has moved by a distance exceeding a predetermined value from the time of pre-shot radiography to the time of obtainment of the slice image.

In the radiography apparatus of the present invention, the slice image obtainment means may obtain the slice image by irradiating the subject with the radiation continuously while the radiation source and the detection means are moved synchronously.

Further, in the radiography apparatus of the present invention, the slice image obtainment means may obtain a plurality of radiographic images corresponding to a plurality of radiation source positions by moving the radiation source, relative to the detection means, to the plurality of radiation source positions and by irradiating the subject with the radiation from the plurality of radiation source positions, and obtain the slice image of the subject by reconstructing the slice image from the plurality of radiographic images.

In this case, the body thickness information obtainment means may obtain the body thickness information about the subject by analyzing the plurality of radiographic images.

Further, in this case, the body thickness information obtainment means may reconstruct an orthogonal slice image from the plurality of radiographic images, the orthogonal slice image representing a slice plane orthogonal to the detection means, and obtain the body thickness information about the subject based on an area in which the subject is present in the orthogonal slice image.

Further, in the radiography apparatus of the present invention, the body thickness information obtainment means may obtain the body thickness information about the subject by detecting the body thickness of the subject.

The radiography apparatus of the present invention may further include a storage means that stores past radiography conditions about a plurality of subjects. Further, the condition setting means may refer to the past radiography conditions stored in the storage means, and set, based on the past radiography condition about the subject to be radiographed, the slice image obtainment condition if the past radiography condition about the subject to be radiographed is stored in the storage means.

According to the present invention, when a slice image is obtained, body thickness information about a subject is obtained, and a slice image obtainment condition representing a range in which the slice image is obtained is set based on the body thickness information. Further, the slice image is obtained based on the set slice image obtainment condition. Therefore, it is possible to efficiently set the slice image obtainment condition that is appropriate for the body thickness of the subject. Hence, it is possible to efficiently obtain the slice image.

Here, pre-shot radiography is performed to set the radiography condition in obtainment of a slice image. Further, when the pre-shot radiography is plain radiography, the pre-shot radiography is necessary to diagnose a patient. Therefore, the pre-shot radiography is always performed before obtainment of the slice image. When the slice image is obtained after pre-shot radiography, it is possible to set a slice image obtainment condition, without irradiating the subject with unnecessary radiation (additional or excessive radiation), by obtaining body thickness information about the subject based on the radiography condition in the pre-shot radiography.

A slice image may be obtained optionally after pre-shot radiography. As the slice image is obtained optionally, especially when the pre-shot radiography is plain radiography, if diagnosis is possible by using only a pre-shot image obtained in the pre-shot radiography, obtainment of the slice image may be omitted. Consequently, it is possible to reduce the dose of radiation irradiating the subject.

Radiography by the radiation source located at a position at which pre-shot radiography was performed may be skipped in obtainment of the slice image, and the pre-shot image may be used as a radiographic image obtained by using the radiation source located at the position at which pre-shot radiography was performed. Consequently, in obtainment of the slice image, radiography by the radiation source located at the position at which pre-shot radiography was performed may be omitted. Hence, it is possible to reduce the dose of radiation irradiating the subject in obtainment of the slice image.

In this case, the movement of the subject may be detected. When the subject has moved by a distance exceeding a predetermined value from the time of pre-shot radiography to the time of obtainment of the slice image, radiography by the radiation source located at the position at which pre-shot radiography was performed may be performed in obtainment of the slice image. Consequently, it is possible to prevent a drop in the image quality caused by a shift in the position of the subject between the radiographic image obtained by using the radiation source located at the position at which pre-shot radiography was performed and radiographic images obtained by using the radiation source located at different positions.

Further, past radiography conditions about a plurality of subjects may be stored in a storage means, and the past radiography conditions stored in the storage means may be referred to. If a past radiography condition about the subject to be radiographed is stored in the storage means, the slice image obtainment condition may be set based on the past radiography condition about the subject to be radiographed. Consequently, it is possible to obtain the slice image by setting the same target of radiography as that of the past radiography. Therefore, it is possible to accurately observe the progress or course of the condition of a patient by using slice images.

BRIEF DESCRIPTION OF THE DRAWINGS

FIG. 3 is a diagram for explaining the position of an X-ray tube in plain radiography and tomosynthesis radiography;

FIG. 4 is a table showing a relationship of a body thickness with the position of the center plain of slice images on which slice images are reconstructed and a reconstruction range;

FIG. 5A is a diagram for explaining a reconstruction range corresponding to a body thickness;

FIG. 5B is a diagram for explaining a reconstruction range corresponding to a body thickness;

FIG. 5C is a diagram for explaining a reconstruction range corresponding to a body thickness;

FIG. 6 is a table showing correlation of a body thickness to a value for correcting the center plain and a value for correcting the reconstruction range;

FIG. 8A is a diagram illustrating an example of a plain image displayed on a display unit;

FIG. 8B is a diagram illustrating an example of a plain image displayed on the display unit;

FIG. 9 is a schematic diagram illustrating the configuration of an X-ray radiography apparatus for performing tomosynthesis radiography to which a radiography apparatus according to a second embodiment of the present invention has been applied;

FIG. 15 is a schematic diagram illustrating the configuration of an X-ray radiography apparatus for performing tomography to which a radiography apparatus according to a fourth embodiment of the present invention has been applied.

DESCRIPTION OF THE PREFERRED EMBODIMENTS

Figure 1:
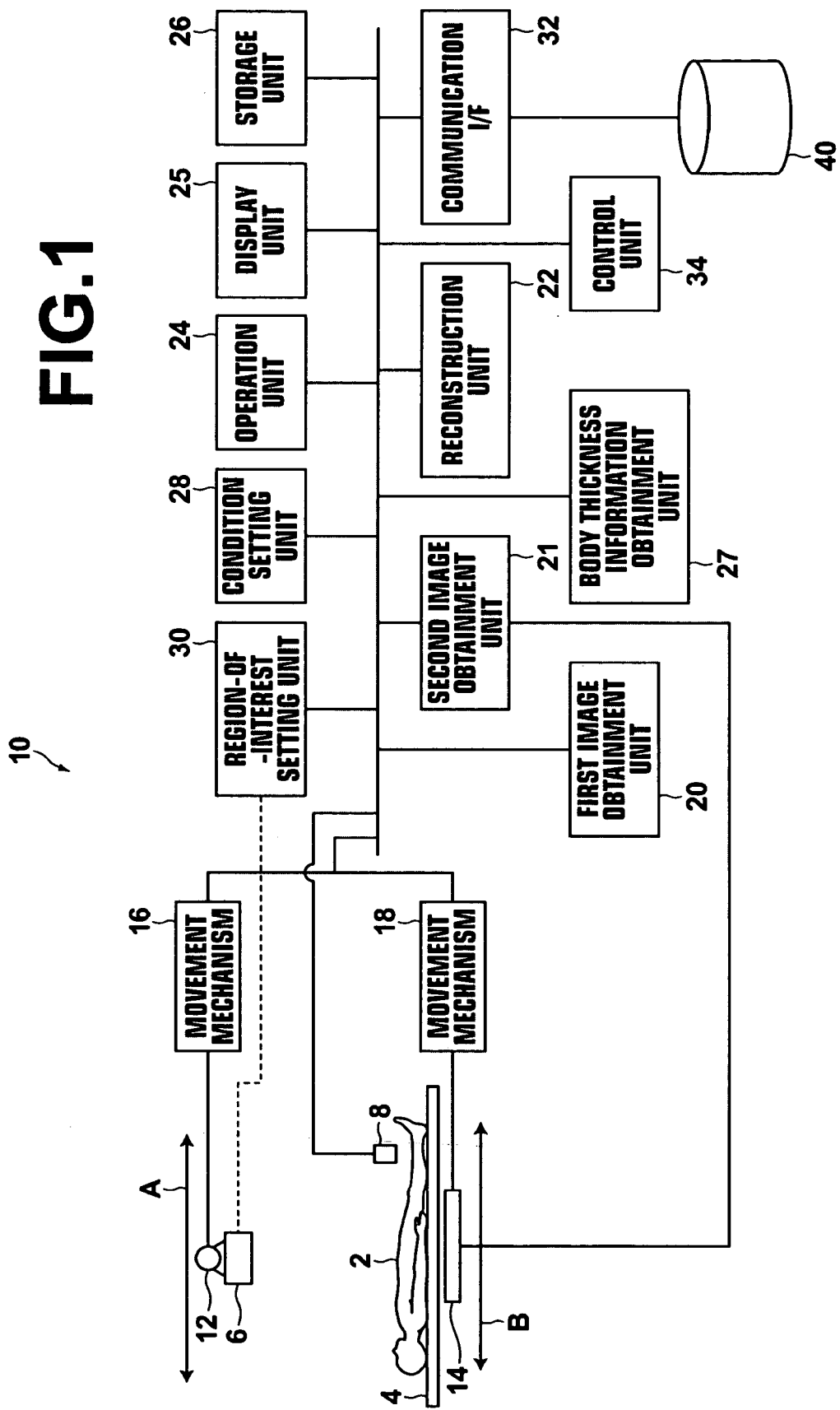
FIG. 1 is a schematic diagram illustrating the configuration of an X-ray radiography apparatus for performing tomosynthesis radiography to which a radiography apparatus according to a first embodiment of the present invention has been applied.

Hereinafter, embodiments of the present invention will be described with reference to drawings. FIG. 1 is a schematic diagram illustrating an X-ray radiography apparatus for performing tomosynthesis radiography to which a radiography apparatus according to a first embodiment of the present invention has been applied. As illustrated in FIG. 1, an X-ray radiography apparatus 10 according to the first embodiment includes an X-ray tube 12 and a flat-panel X-ray detector (hereinafter, simply referred to as a detector) 14. The X-ray tube 12 is moved straight or along an arc or curve by a movement mechanism 16. The X-ray tube 12 outputs, at a plurality of positions on the movement path thereof, X-rays to a subject 2 on the top board 4 of a radiographic table. In the first embodiment, it is assumed that the X-ray tube 12 moves along a straight line in the direction of arrow A. The dose of radiation of X-rays output to the subject 2 is controlled by a condition setting unit 28, which will be described later, so that the dose of radiation becomes a predetermined value. Further, a collimator (a diaphragm for changing an irradiation field size) 6 is connected to the X-ray tube 12 so that an operator can set the range of the subject 2 irradiated with radiation.

The detector 14 is arranged in such a manner to face the X-ray tube 12 with the top board 4 of the radiographic table, on which the subject 2 is placed, therebetween. The detector 14 is arranged so as to detect X-rays that have passed through the subject 2. The detector 14 is moved straight or in an arc or curve as necessary by a movement mechanism 18, and detects X-rays that have passed through the subject 2 at a plurality of positions on the movement path of the detector 14. In the present embodiment, it is assumed that the detector 14 is moved in the direction of arrow B along a straight line.

Further, the X-ray radiography apparatus 10 includes a first image obtainment unit 20. The first image obtainment unit 20 fixes the X-ray tube 12 to a predetermined radiation source position. At the predetermined radiation source position, a perpendicular to the detector 14 that passes through the center of gravity of the detector 14 intersects the movement path of the X-ray tube 12 at right angles. Further, X-rays are output from the predetermined radiation source position to the subject 2, and the X-rays that have passed through the subject 2 are detected by the detector 14. Accordingly, a plain radiographic image is obtained by performing plain radiography by the X-ray tube 12 located at the predetermined radiation source position.

Further, the X-ray radiography apparatus 10 includes a second image obtainment unit 21 and a reconstruction unit 22. The second image obtainment unit 21 performs tomosynthesis radiography by moving the X-ray tube 12 on the movement path of the X-ray tube 12, and by irradiating the subject 2 with X-rays at different angles. Further, X-rays that have passed through the subject 2 are detected by the detector 14. Accordingly, a plurality of radiographic images are obtained by using the radiation source located at the plurality of positions during movement of the radiation source. The reconstruction unit 22 reconstructs a slice image representing a desired slice plane of the subject from a plurality of radiographic images for tomosynthesis (hereinafter, simply referred to as radiographic images) that have been obtained by the second image obtainment unit 21. Next, a method for reconstructing a slice image will be described.

Figure 2:
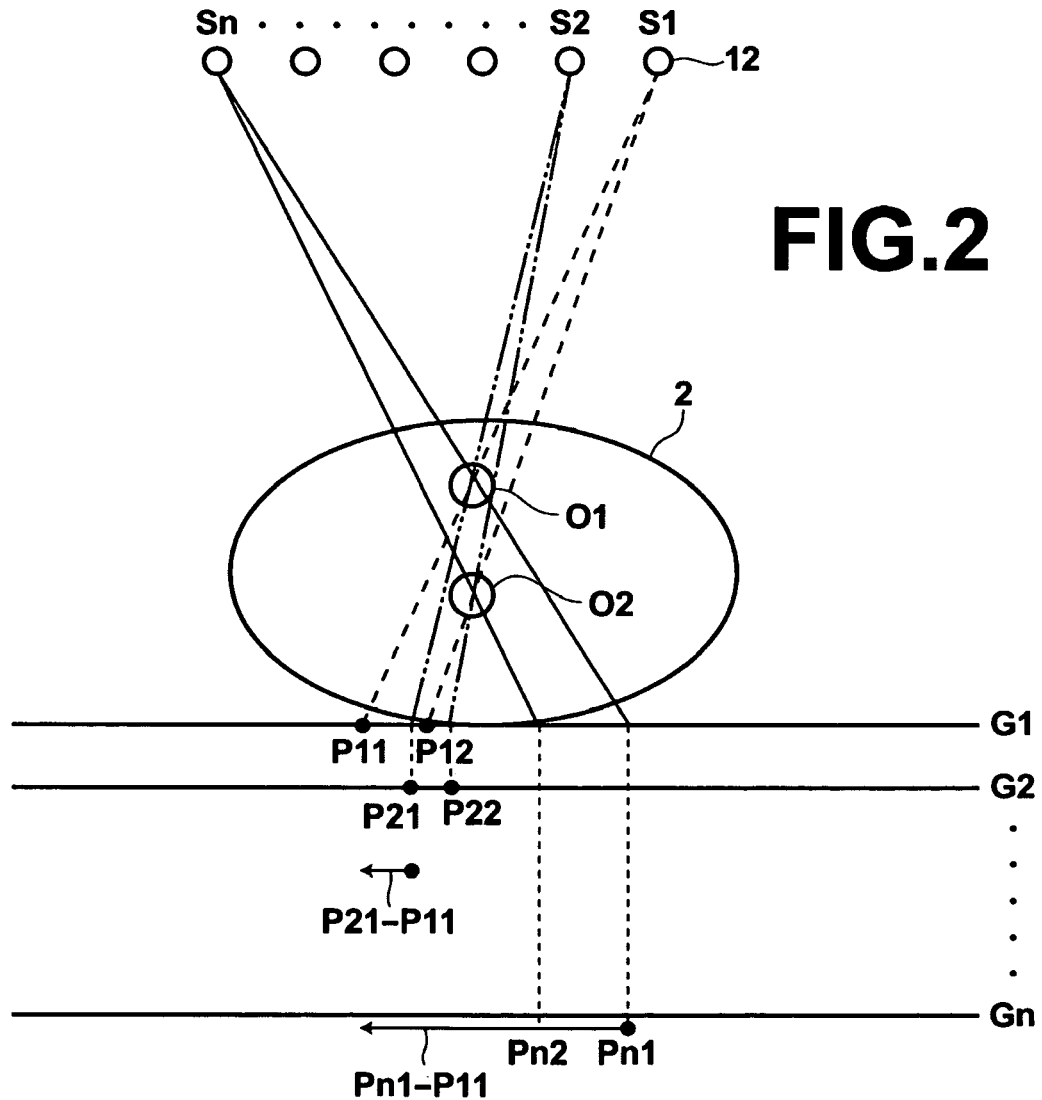
FIG. 2 is a diagram for explaining tomosynthesis radiography.

As illustrated in FIG. 2, when the X-ray tube 12 is moved to each position S1, S2, ..., Sn, and radiography is performed on the subject 2 from different irradiation angles, it is assumed that radiographic images G1, G2, ..., Gn are obtained when the X-ray tube 12 are located at positions S1, S2, ..., Sn, respectively. For example, when objects (O1, O2), which are located in a subject 2 at different depths from each other, are projected from position S1, at which the X-ray tube 12 is located, the objects (O1, O2) are projected to positions P11 and P12 in the radiographic image G1, respectively. Further, when the objects (O1, O2) are projected from position S2, at which the X-ray tube 12 is located, the objects (O1, O2) are projected to positions P21 and P22 in the radiographic image G2, respectively. In this way, when projection of the objects (O1, O2) is repeated from different positions S1, S2, ..., Sn, at which the X-ray tube 12 is located, object O1 is projected to positions P11, P21, ..., Pn1, respectively, and object O2 is projected to positions P12, P22, ..., Pn2, respectively, in such a manner to correspond to the positions of the radiation source (X-ray tube 12).

When the cross section on which the object O1 is present should be emphasized, the radiographic image G2 is moved by P21-P11, the radiographic image G3 is moved by P31-P11, ..., the radiographic image Gn is moved by Pn1-P11, and the moved radiographic images are added to generate a slice image in which a structure on the cross section at the depth of the object O1 is emphasized. Further, when the cross section on which the object O2 is present should be emphasized, the radiographic image G2 is moved by P22-P12, the radiographic image G3 is moved by P32-P12, ..., the radiographic image Gn is moved by Pn2-P12, and the moved radiographic images are added. As described above, it is possible to obtain an image in which a slice image at a desired position is emphasized by matching the positions of the radiographic images G1, G2, ..., Gn based on the position of a necessary slice plane and by adding the radiographic images G1, G2, ..., Gn.

As illustrated in FIG. 3, in the present embodiment, the intersection of a perpendicular to the detector 14 that passes through the center of gravity of the detector 14 and the movement path of the X-ray tube 12 is used as a predetermined radiation source position Sc. When the first image obtainment unit 20 performs plain radiography, the X-ray tube 12 is fixed to the predetermined radiation source position Sc. When the second image obtainment unit 21 performs tomosynthesis radiography, radiography is performed at a plurality of radiation source positions S1 through Sn. However, since a plain radiographic image has been obtained at the predetermined radiation source position Sc, the plain radiographic image may be used to reconstruct a slice image. Therefore, in the present embodiment, when tomosynthesis radiography is performed, radiography at predetermined radiation source position Sc may be skipped, and the plain radiographic image obtained at the predetermined radiation source Sc may be used, as a radiographic image at the predetermined radiation source position Sc.

However, if the subject 2 has moved from the time of plain radiography to the time of tomosynthesis radiography, the position of the subject 2 included in the plain radiographic image and the position of the subject included in the plurality of radiographic images are shifted from each other. Therefore, when the plain radiographic image obtained at the predetermined radiation source position Sc is used to reconstruct a slice image, it is impossible to accurately reconstruct the slice image. Therefore, the X-ray radiography apparatus 10 includes a detection unit (subject-movement detection unit) 8 that detects the movement of the subject 2. The detection unit 8 includes a sensor, such as an ultrasonic sensor and an infrared ray sensor. The detection unit 8 detects the movement of the subject 2 from a position at which the subject is located at the time of plain radiography to a position at which the subject is located at the time of tomosynthesis radiography, and outputs the result of detection to the second image obtainment unit 21. The second image obtainment unit 21 judges, based on the detection result by the detection unit 8, whether the plain radiographic image obtained at the predetermined radiation source position Sc should be used to reconstruct the slice image.

Specifically, the second image obtainment unit 21 judges whether the subject 2 has moved from the time of plain radiography to the time of tomosynthesis radiography by a value greater than or equal to a predetermined threshold value. If the judgment is NO, radiography at the predetermined radiation source position Sc is skipped, because the plain radiographic image obtained at the predetermined radiation source position Sc is used to reconstruct a slice image. In contrast, if the judgment is YES, radiography is performed also at the predetermined radiation source position Sc, because the subject 2 has moved.

Further, the X-ray radiography apparatus 10 includes an operation unit 24, a display unit 25 and a storage unit 26. The operation unit 24 includes an input device, such as a keyboard, a mouse and a touch-panel-type device, and receives an instruction (information) for operating the X-ray radiography apparatus 10 from an operator. In the present embodiment, each unit of the X-ray radiography apparatus 10 operates based on the information input by the operator at the operation unit 24. The display unit 25 is a display device, such as a liquid crystal monitor. The display unit 25 displays a plain radiographic image obtained by the first image obtainment unit 20, and a slice image reconstructed by the reconstruction unit 22. Further, the display unit 25 displays a message necessary for operation, and the like. The storage unit 26 stores various kinds of parameters, a table, or the like that are necessary to operate the X-ray radiography apparatus 10.

Further, the X-ray radiography apparatus 10 includes a body thickness information obtainment unit 27 and a condition setting unit 28. The body thickness information obtainment unit 27 obtains body thickness information representing the body thickness of the subject 2. The condition setting unit 28 sets the radiography condition in plain radiography and the radiography condition in tomosynthesis radiography. Further, the condition setting unit 28 sets, based on the body thickness information obtained by the body thickness information obtainment unit 27, slice image obtainment condition representing a range that is the target of generating a slice image in the subject 2. First, the condition setting unit 28 sets, as the radiography condition in plain radiography, the tube voltage of the X-ray tube 12 and the dose of radiation irradiating the subject 2 in plain radiography. The condition setting unit 28 may set, as the radiography condition, a tube voltage and the dose of radiation that correspond to a region to be radiographed that has been input by an operator. Alternatively, the condition setting unit 28 may directly set, as the radiography condition, the tube voltage and the dose of radiation that have been input by the operator. The condition setting unit 28 stores the set radiography condition in the storage unit 26. The condition setting unit 28 stores, as the radiography condition in plain radiography, at least one of the distribution range of pixel values of a plain radiographic image obtained in plain radiography, an exposure amount of a portion in the plain radiographic image obtained by plain radiography, the portion being directly irradiated with radiation (the exposure amount may be obtained based on pixel values), an exposure time period when automatic exposure control has been performed in plain radiography, and the like in the storage unit 26.

In the present embodiment, first, plain radiography is performed to obtain a plain radiographic image, and the plain radiographic image is displayed on the display unit 25 to diagnose a patient. Further, when it is necessary to further diagnose the patient, tomosynthesis radiography is performed. For example, when a suspected fracture of bone is not confirmed by using the plain radiographic image, tomosynthesis radiography is performed. Therefore, when the operator has instructed tomosynthesis radiography after plain radiography, the body thickness information obtainment unit 27 obtains body thickness information about the subject 2 based on the radiography condition stored in the storage unit 26. Specifically, the body thickness information obtainment unit 27 obtains the body thickness information about the subject 2 based on at least one of the dose of radiation in the plain radiography, the tube voltage in the plain radiography, the distribution range of pixel values in a plain radiographic image, and the like. When the dose of radiation is higher, or the tube voltage is higher, or the distribution range of pixel values is larger, the body thickness of the subject 2 is thicker. In contrast, when the dose of radiation is lower, or the tube voltage is lower, or the distribution range of pixel values is smaller, the body thickness of the subject 2 is thinner. Therefore, the condition setting unit 28 compares the dose of radiation, the tube voltage or the distribution range of pixel values with respective predetermined threshold values. The condition setting unit 28 judges whether the body thickness of the subject 2 is thick, standard, or thin based on whether the dose of radiation, the tube voltage or the distribution range of pixel values is greater than respective predetermined threshold values.

The condition setting unit 28 sets the slice image obtainment condition representing a range that is the target of generating the slice image in the subject 2 based on the body thickness information. In the present embodiment, the position of the center plane of slice planes in the depth direction of the subject 2 and the reconstruction range of slice images based on the position of the center plane are set as the slice image obtainment condition.

Therefore, in the first embodiment, the storage unit 26 stores a table in which the relationship of the body thickness with the position of the center plane of slice planes on which slice images are reconstructed and the reconstruction range is regulated. FIG. 4 is a table in which the relationship of the body thickness with the position of the center plane of slice planes on which slice images are reconstructed and the reconstruction range is regulated. As illustrated in FIG. 4, Table T1 correlates a thick body thickness to 15 cm as the position of the center plane, and 20 cm as the reconstruction range. Table T1 correlates a standard body thickness to 10 cm as the position of the center plane, and 10 cm as the reconstruction range. Further, Table T1 correlates a thin body thickness to 5 cm as the position of the center plane, and 5 cm as the position of the reconstruction range. Here, the position of the center plane is represented by a distance from the top board 4 of the radiographic table. Therefore, as illustrated in FIGS. 5A through 5C, the position of center plane X0 and reconstruction range R0 are set for each of subjects 2A, 2B and 2C based on the respective body thicknesses of the subjects. FIG. 5A illustrates the subject 2A, which has a thick body thickness. FIG. 5B illustrates the subject 2B, which has a standard body thickness. FIG. 5C illustrates the subject 2C, which has a thin body thickness.

It is not necessary that the table regulates the position of the center plane and the reconstruction range as illustrated in FIG. 4. For example, as table T2 illustrated in FIG. 6 shows, a value for correcting the position of the center plane and a value for correcting the reconstruction range based on the body thickness may be regulated. The value for correcting the reconstruction range is used to correct the thickness of the reconstruction range that has been set in advance for the standard body thickness.

Further, the condition setting unit 28 sets, as the radiography condition in tomosynthesis radiography, the dose of radiation at each of radiation source positions in tomosynthesis radiography. The condition setting unit 28 sets the radiography condition in tomosynthesis radiography in such a manner that the dose of X-rays irradiating the subject 2 in tomosynthesis radiography is N times larger than the dose of radiation in plain radiography (the number of radiation source positions=N). Alternatively, the radiography conditions in tomosynthesis radiography may be set by the operator by using the operation unit 24.

Further, the condition setting unit 28 sets, as the radiography condition in tomosynthesis radiography, a slice angle in tomosynthesis radiography. The term "slice angle" refers to an angle formed, at a base point on a base plane, by two lines connecting the base point and end points defining the movement range of the X-ray tube 12. The base plane is a detection surface of the detector 14, the top surface of the top board 4 of the radiographic table, a surface or plane in the reconstruction range that is closest to the detection surface of the detector 14, or the like, which defines the range of obtaining slice images. In FIG. 3, when the top surface of the top board 4 of the radiographic table is the base plane, and the intersection of the top surface of the top board 4 and a perpendicular to the detector 14 that passes through the center of gravity of the detector 14 is the base point, the slice angle is represented by θ.

Further, the radiography apparatus 10 includes a region-of-interest setting unit 30. When ordinary tomosynthesis radiography is performed, an operator sets, as a reconstruction range, the range of the subject 2 in the depth direction thereof (for example the range of heights from the top plate of the radiographic table) by using the operation unit 24. Further, the operator sets, as a range to be irradiated with X-rays, a range in a plane orthogonal to the depth direction by using a collimator 6. However, in the present embodiment, the range in the depth direction in tomosynthesis radiography, in other words, the reconstruction range is set by the condition setting unit 28. Therefore, in the present embodiment, the operator sets only the range in a plane orthogonal to the depth direction, in other words, only the range to be irradiated with X-rays. When the range to be irradiated with X-rays is set by using the collimator 6, visible light is output to the subject 2 through the collimator 6 instead of X-rays. Accordingly, the operator can set the range to be irradiated with X-rays by adjusting the range of visible light irradiating the subject 2 by using the collimator 6. The region-of-interest setting unit 30 sets a three-dimensional region of interest based on the reconstruction range of the subject 2 that has been set by the condition setting unit 28 and the range to be irradiated with X-rays that has been set by the operator by using the collimator 6.

Further, the X-ray radiography apparatus 10 includes a communication interface (I/F) 32 for connecting the X-ray radiography apparatus to an external server 40 through a network. The external server 40 stores plain radiographic images and slice images about a plurality of subjects that were obtained in past radiography, and that were sent to the external server 40. Further, information, such as the position of the center plane in tomosynthesis radiography, the reconstruction range, the irradiation range of X-rays, and the slice angle, is sent to the external server 40 as reference information. The external server 40 correlates a plain radiographic image of a subject, slice images of the subject, reference information, and a subject ID for identifying the subject to each other, and stores them.

Further, the X-ray radiography apparatus 10 includes a control unit 34 for controlling each unit of the X-ray radiography apparatus 10. The control unit 34 controls each unit of the X-ray radiography apparatus 10 based on an instruction from the operation unit 24.

Figure 7:
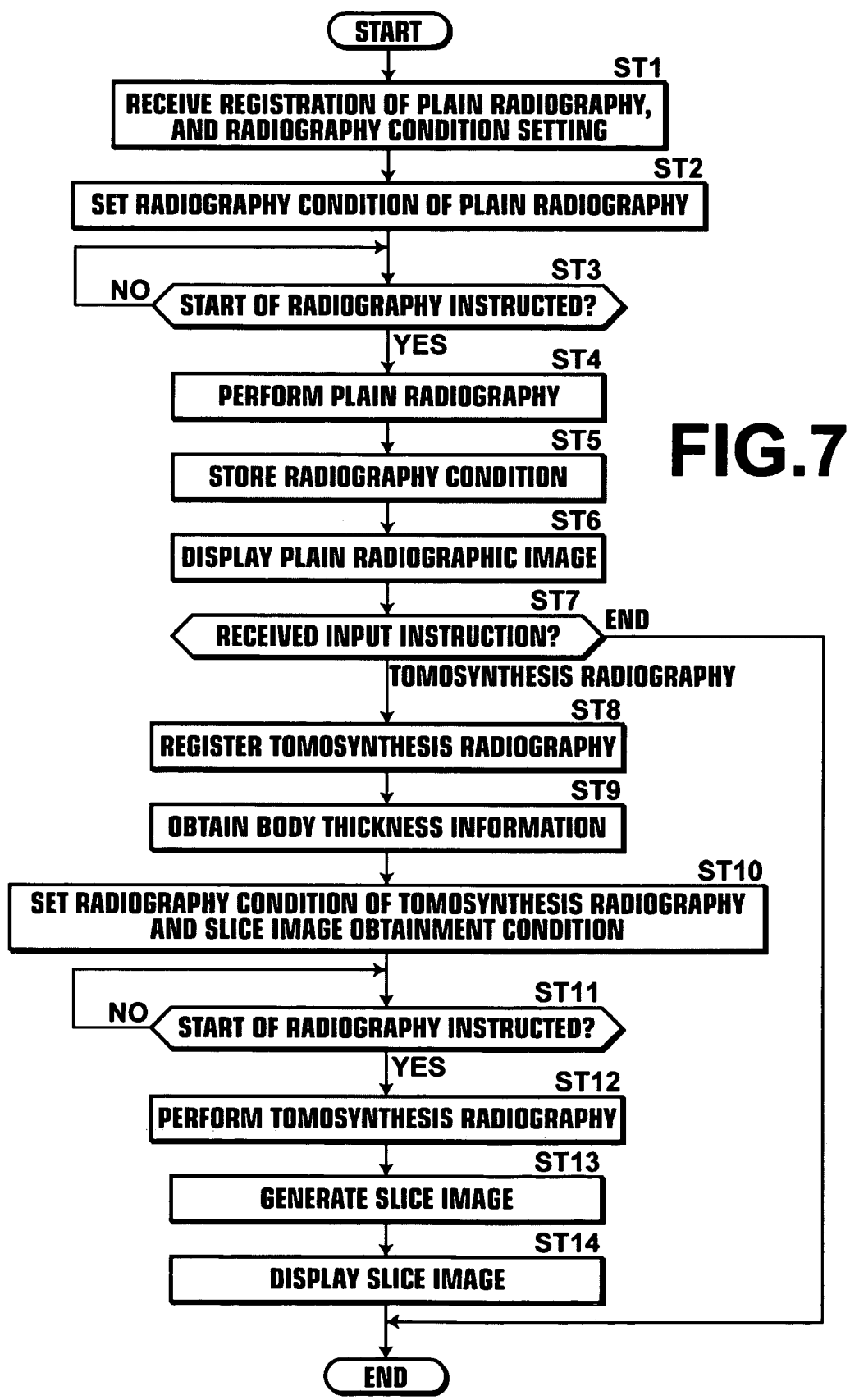
FIG. 7 is a flowchart showing process performed in the first embodiment of the present invention.

Next, the process performed in the first embodiment will be described. FIG. 7 is a flow chart illustrating the process performed in the first embodiment. In the description of the first embodiment, it is assumed that the radiography condition in plain radiography is input by an operator. However, the method for setting the radiography condition in plain radiography is not limited. As described above, the radiography condition may be set based on information, such as region to be radiographed, which is input by the operator. Further, it is assumed that the detector 14 is not moved, and only the X-ray tube 12 is moved to perform tomosynthesis radiography. First, the control unit 34 receives registration of plain radiography, as radiography for diagnosis to be performed, and setting of radiography condition in plain radiography by the operator from the operation unit 24 (step ST1). Accordingly, the control unit 34 registers the plain radiography, as the radiography for diagnosis to be performed, in the X-ray radiography apparatus 10, and the condition setting unit 28 sets the radiography condition for plain radiography (step ST2). When the operator inputs an instruction for starting radiography (step ST3 is YES), the first image obtainment unit 20 performs plain radiography, and obtains a plain radiographic image (step ST4). After the plain radiography, the condition setting unit 28 stores the radiography condition of the plain radiography in the storage unit 26 (step ST5).

Next, the control unit 34 displays a plain radiographic image obtained by the plain radiography on the display unit 25 (step ST6). FIGS. 8A and 8B are diagrams illustrating examples of the manner of displaying a plain radiographic image. As illustrated in FIG. 8A, the control unit 34 displays a confirmation screen 50 including plain radiographic image G0 and message M0, asking whether tomosynthesis radiography should be performed, on the display unit 25. The operator observes the displayed plain radiographic image, and performs diagnosis. Further, the operator judges whether tomosynthesis radiography is necessary, and inputs an instruction (YES or NO) as to whether tomosynthesis radiography should be performed by using the operation unit 24. Therefore, the control unit 34 receives the instruction input by the operator (step ST7). When the input instruction is an instruction for ending diagnosis, in other words, when the input is NO, processing ends. Instead of the confirmation screen 50, a confirmation screen 51, as illustrated in FIG. 8B may be displayed on the display unit 25. The confirmation screen 51 includes an execution button 52 for making the X-ray radiography apparatus 10 perform tomosynthesis radiography. In this case, the operator should operate the execution button 52 only when tomosynthesis radiography is necessary.

In contrast, when the input instruction is an instruction for performing tomosynthesis radiography, in other words, when the input is YES, the control unit 34 registers tomosynthesis radiography, as radiography for diagnosis to be performed (step ST8). The body thickness information obtainment unit 27 obtains body thickness information about the subject 2 based on the radiography condition in plain radiography that is stored in the storage unit 26 (step ST9). The condition setting unit 28 sets radiography condition in tomosynthesis radiography. Further, the condition setting unit 28 sets, based on the body thickness information, slice image obtainment condition representing a range that is a target of generating a slice image in the subject 2 (step ST10). When the operator inputs an instruction for starting radiography (step ST11 is YES), the second image obtainment unit 21 performs tomosynthesis radiography to obtain a plurality of radiographic images (step ST12). At this time, judgment is made as to whether the subject 2 has moved by a distance exceeding a predetermined threshold value from the time of the plain radiography to the time of tomosynthesis radiography. If it is judged that the subject 2 has not moved by a distance exceeding the predetermined threshold value, radiography is not performed on the subject 2 at the predetermined radiation source position Sc. Further, the reconstruction unit 22 reconstructs a slice image from a plurality of radiographic images to obtain the slice image in the range represented by the slice image obtainment condition (step ST13). The control unit 34 displays the slice image on the display unit 25 (step ST14), and processing ends. The reconstructed slice image is stored in a storage apparatus, such as an HDD (hard disk drive), which is not illustrated. Alternatively, the reconstructed slice image is sent to the server 40 through a network.

As described above, in the first embodiment, the body thickness information about the subject 2 is obtained, and the range that is the target of generating the slice image in the subject 2 is set based on the body thickness information. The range that is the target of generating the slice image is the slice image obtainment condition representing a reconstruction range, in which a slice image is reconstructed, and the position of the center plane of the reconstruction range. Therefore, it is possible to efficiently set the slice image obtainment condition based on the body thickness of the subject 2. Hence, it is possible to efficiently obtain the slice image.

In the first embodiment, when tomosynthesis radiography is performed after plain radiography, the body thickness of the subject 2 is set in tomosynthesis radiography based on the radiography condition in the plain radiography. Since plain radiography is necessary to diagnose the subject 2, the plain radiography is always performed before tomosynthesis radiography. Therefore, according to the first embodiment, it is possible to set the slice image obtainment condition without irradiating the subject 2 with unnecessary radiation.

Further, after plain radiography, tomosynthesis radiography is optionally performed. Therefore, when diagnosis is possible by using only the plain radiographic image obtained by plain radiography, tomosynthesis radiography may be omitted. Consequently, it is possible to reduce the dose of radiation irradiating the subject.

Further, in tomosynthesis radiography, radiography at the predetermined radiation source position Sc may be omitted by skipping radiography at the predetermined radiation source position Sc, and a plain radiographic image may be used as a radiographic image at the predetermined light source position Sc. Consequently, it is possible to reduce the dose of radiation irradiating the subject in tomosynthesis radiography.

In this case, the detection unit 8 may detect the movement of the subject 2. When the subject 2 has moved by a distance exceeding a predetermined threshold value from the time of plain radiography to the time of tomosynthesis radiography, radiography is performed by the X-ray tube 12 located at the predetermined radiation source position Sc in tomosynthesis radiography. Hence, it is possible to prevent a drop in the image quality of slice images that is caused by a shift in the position of the subject 2 from the position in the radiographic image obtained at the predetermined radiation source position Sc to positions in radiographic images obtained at other radiation source positions.

In the first embodiment, after the plain radiographic image is displayed, tomosynthesis radiography is performed by an instruction by the operator. Alternatively, the operator may input an instruction of tomosynthesis radiography, after the plain radiographic image is displayed and a region of interest is set. After the plain radiographic image is displayed, the operator may set, as a region of interest, a region in which tomosynthesis radiography is desired by using the operation unit 24. Further, the second image obtainment unit 21 may perform tomosynthesis radiography by detecting that the operator has set the region of interest. In this case, the condition setting unit 28 sets, based on the region of interest set by the operator in the plain radiographic image, the range of irradiation with X-rays. Further, the second image obtainment unit 21 performs tomosynthesis radiography based on the set range of irradiation with X-rays.

In the first embodiment, when plain radiography is performed, the condition setting unit 28 may judge, with respect to the subject ID of the subject 2 to be radiographed, whether a plain radiographic image or a slice image obtained in past diagnosis is stored in the server 40. If the judgment is YES, reference information corresponding to the subject ID may be obtained from the server 40. Further, slice image obtainment condition may be set by using the reference information. In this case, after plain radiography for the present diagnosis is performed, the condition setting unit 28 may set the range of irradiation with X-rays by using the plain radiographic image and the reference information. The range of irradiation with X-rays may be set so that slice images in the same range as the range of the slice images obtained in the past diagnosis (diagnoses) are obtained. Specifically, the condition setting unit 28 identifies the range of irradiation with X-rays in a plain radiographic image obtained in the past diagnosis by using the plain radiographic image obtained in the past diagnosis and reference information. Further, the condition setting unit 28 obtains a correlation between the range of irradiation with X-rays and the plain radiographic image obtained in the present diagnosis. Accordingly, a region corresponding to the range of irradiation with radiation in the past radiography is set in the plain radiographic image obtained in the present diagnosis. Further, a region corresponding to the region set in the plain radiographic image obtained in the present diagnosis is set as the region of radiation with X-rays in tomosynthesis radiography in the present diagnosis. The position of the center plane of slice planes and the reconstruction range may be set to be the same as the reference information. Alternatively, the position of the center plane of slice planes and the reconstruction range may be set in a manner similar to the first embodiment by using the plain radiographic image obtained in the present diagnosis.

In the first embodiment, plain radiography is performed before tomosynthesis radiography. Further, the slice image obtainment condition is set by obtaining body thickness information by using the radiography condition in the plain radiography. Alternatively, pre-shot radiography for determining the radiography condition in tomosynthesis radiography may be performed without performing plain radiography. Further, the slice image obtainment condition may be set by obtaining the body thickness information about the subject 2 by using the radiography condition in the pre-shot radiography. In this case, if the pre-shot image is used to reconstruct a slice image, it is not necessary to perform radiography by the X-ray tube 12 located at the predetermined radiation position Sc, at which pre-shot radiography was performed, in tomosynthesis radiography. Therefore, it is possible to reduce the dose of radiation irradiating the subject in tomosynthesis radiography.

Next, a second embodiment of the present invention will be described. FIG. 9 is a schematic diagram illustrating the configuration of an X-ray radiography apparatus for performing tomosynthesis radiography to which a radiography apparatus according to the second embodiment of the present invention has been applied. In the second embodiment, the same reference numerals are assigned to the same elements as the elements of the first embodiment, and detailed descriptions of the elements are omitted. An X-ray radiography apparatus 10A of the second embodiment differs from the first embodiment in that the body thickness information obtainment unit 27A obtains body thickness information about the subject 2 by analyzing a plurality of radiographic images obtained by tomosynthesis radiography. The process performed by the body thickness information obtainment unit 27A in the second embodiment will be described.

Figure 10:
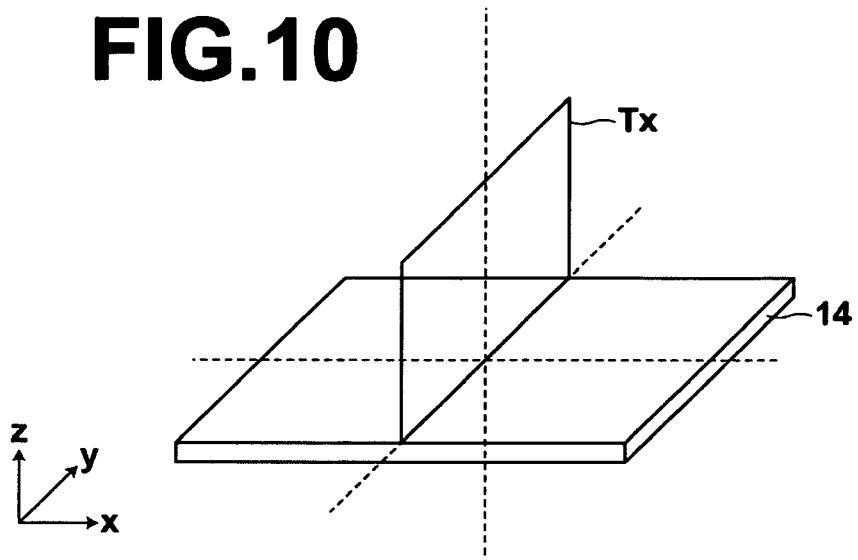
FIG. 10 is a diagram for explaining obtainment of body thickness information in the second embodiment.
Figure 11:
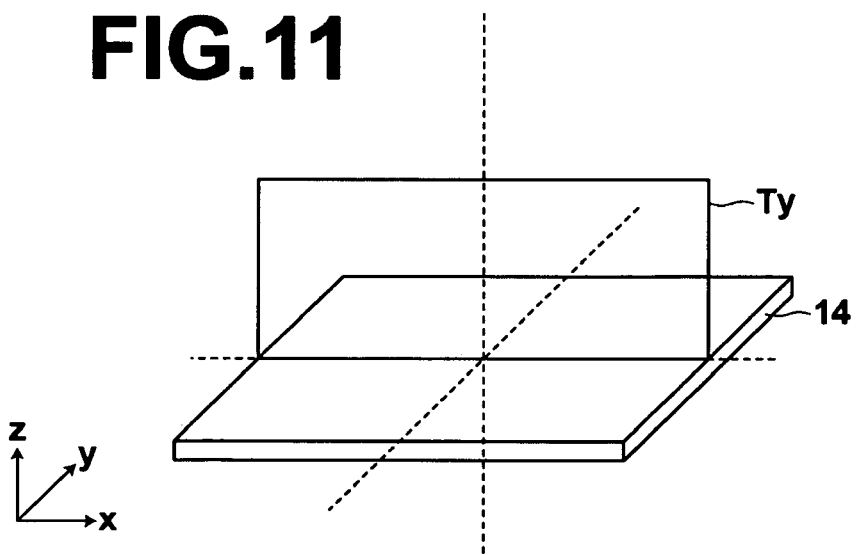
FIG. 11 is a diagram for explaining obtainment of body thickness information in the second embodiment.

First, the body thickness information obtainment unit 27A reconstructs a slice image from a plurality of radiographic images obtained by tomosynthesis radiography. The body thickness information obtainment unit 27A generates the slice image representing a slice plane orthogonal to the detection surface of the detector 14 (hereinafter, referred to as an "orthogonal slice image"). For example, when the movement direction of the X-ray tube illustrated in FIG. 9 is direction x, the direction perpendicular to the paper surface of FIG. 9 is direction y, and the vertical direction on the paper surface of FIG. 9 is direction z, slice image Tx is reconstructed as an orthogonal slice image, as illustrated in FIG. 10, or slice image Ty is reconstructed as an orthogonal slice image, as illustrated in FIG. 11. The slice image Tx represents a slice plane on plane yz, which is on the center of gravity of the detection surface of the detector 14. The slice image Ty represents a slice plane on plane xz, which is on the center of gravity of the detection surface of the detector 14. The pixel value Tx (y, z) of each pixel of the slice image Tx and the pixel value Ty (x, z) of each pixel of the slice image Ty may be obtained by adding pixel value P (ti, si) at projection position (ti, si) of point (x, y, z) on the respective slice planes onto i-th radiographic image (i=1 through N). Specifically, the pixel value Tx (y, z) on the slice image Tx may be calculated by using the following formula (1). Further, the orthogonal slice image may be reconstructed by the reconstruction unit 22.

[Formula 1]

$$T_x(y, z) = \sum_{i=l}^{N} P_i(t_i, s_i) = \sum_{i=1}^{N} P_i\left(x * \frac{sz_i}{sz_i - z} - sx_i * \frac{z}{sz_i - z},\ y * \frac{sz_i}{sz_i - z} - sy_i * \frac{z}{sz_i - z}\right) \quad (1)$$

Next, the body thickness information obtainment unit 27A identifies a region of the subject 2 included in the orthogonal slice image. For example, the body thickness information obtainment unit 27A extracts an edge included in the orthogonal slice image by using an edge extraction filter, such as Sobel filter, and identifies, as the region of the subject 2, an area in which a structure specified by the edge is present. Here, the body thickness information obtainment unit 27A may extract only an intense edge of a structure, such as bones, the output value of which from the filter is large. Further, the body thickness information obtainment unit 27A may identify, as the region of the subject 2, the area in which the structure of the subject 2, such as bones, which is specified by the intense edge is present. Further, the body thickness information obtainment unit 27A obtains, as the body thickness information about the subject 2, the length of the identified region in z direction. In the second embodiment, the condition setting unit 28 sets the slice image obtainment condition based on the body thickness information in a manner similar to the first embodiment.

Figure 12:
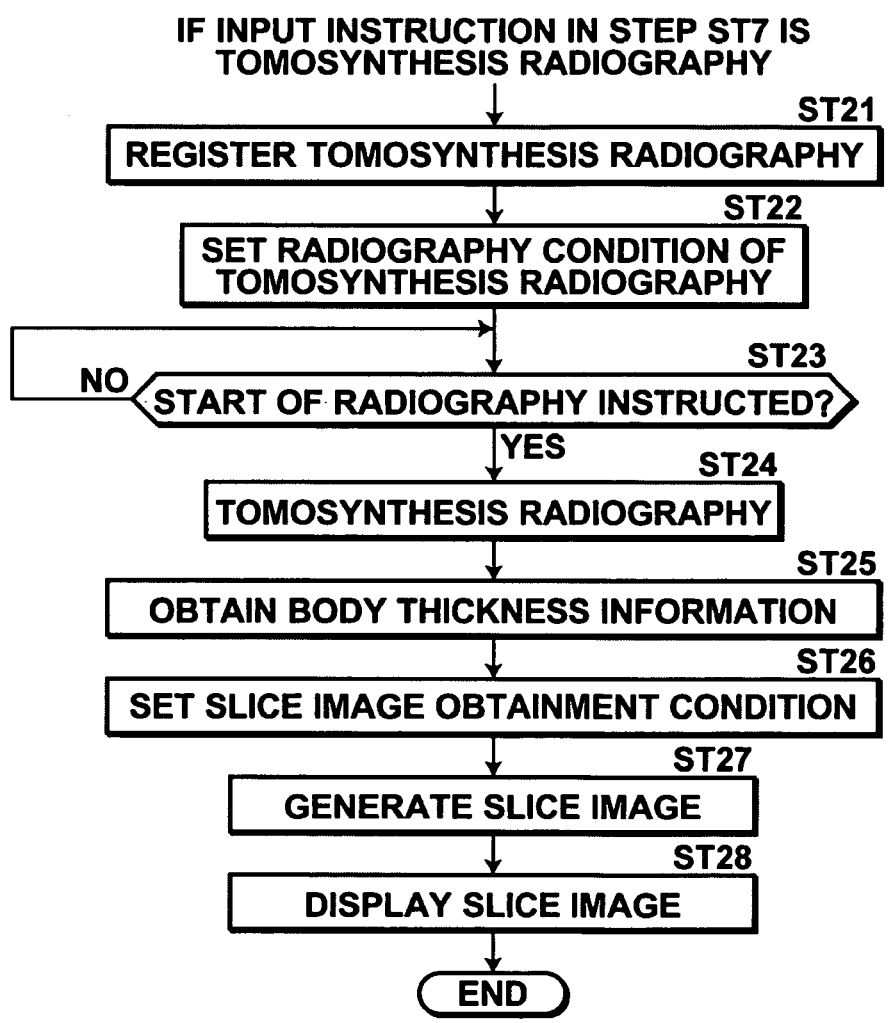
FIG. 12 is a flow chart showing process performed in the second embodiment of the present invention.

Next, the processing performed in the second embodiment will be described. FIG. 12 is a flow chart illustrating the process performed in the second embodiment. In the second embodiment, only the process in step ST8 and thereafter differs from the process illustrated in the flow chart of FIG. 7 in the first embodiment. Therefore, only the process in step ST8 and thereafter will be described.

In the flow chart illustrated in FIG. 7, if the input in step ST7 is YES (tomosynthesis radiography), the control unit 34 registers, as diagnosis to be performed, tomosynthesis radiography (step ST21). Further, the condition setting unit 28 sets the radiography condition of the tomosynthesis radiography (step ST22). When the operator inputs a radiography start instruction (step ST23 is YES), the second image obtainment unit 21 performs tomosynthesis radiography, and obtains a plurality of radiographic images (step ST24). At this time, judgment is made as to whether the subject 2 has moved by a distance exceeding a predetermined threshold value from the time of plain radiography to the time of tomosynthesis radiography. If the subject 2 has not moved by the distance exceeding the predetermined threshold value, radiography is not performed on the subject 2 at the predetermined radiation source position Sc.

Next, the body thickness information obtainment unit 27A obtains body thickness information about the subject 2 by analyzing the plurality of radiographic images (step ST25). Further, the condition setting unit 28 sets, based on the body thickness information, slice image obtainment condition. The slice image obtainment condition represents a range that is the target of generating a slice image in the subject 2 (step ST26).

Further, the reconstruction unit 22 generates a slice image by reconstructing the slice image from the plurality of radiographic images so that the slice image in the range represented by the slice image obtainment condition is obtained (step ST27). The control unit 34 displays the slice image on the display unit 25 (step ST28), and processing ends. The generated slice image is stored in a storage device, such as a HDD, which is not illustrated. Alternatively, the generated slice image may be sent to a server 40 through a network.

As described above, the slice image obtainment condition is set based on the body thickness information also in the second embodiment. Therefore, it is possible to efficiently set the slice image obtainment condition based on the body thickness of the subject 2. Hence, it is possible to efficiently obtain the slice image.

Figure 13:
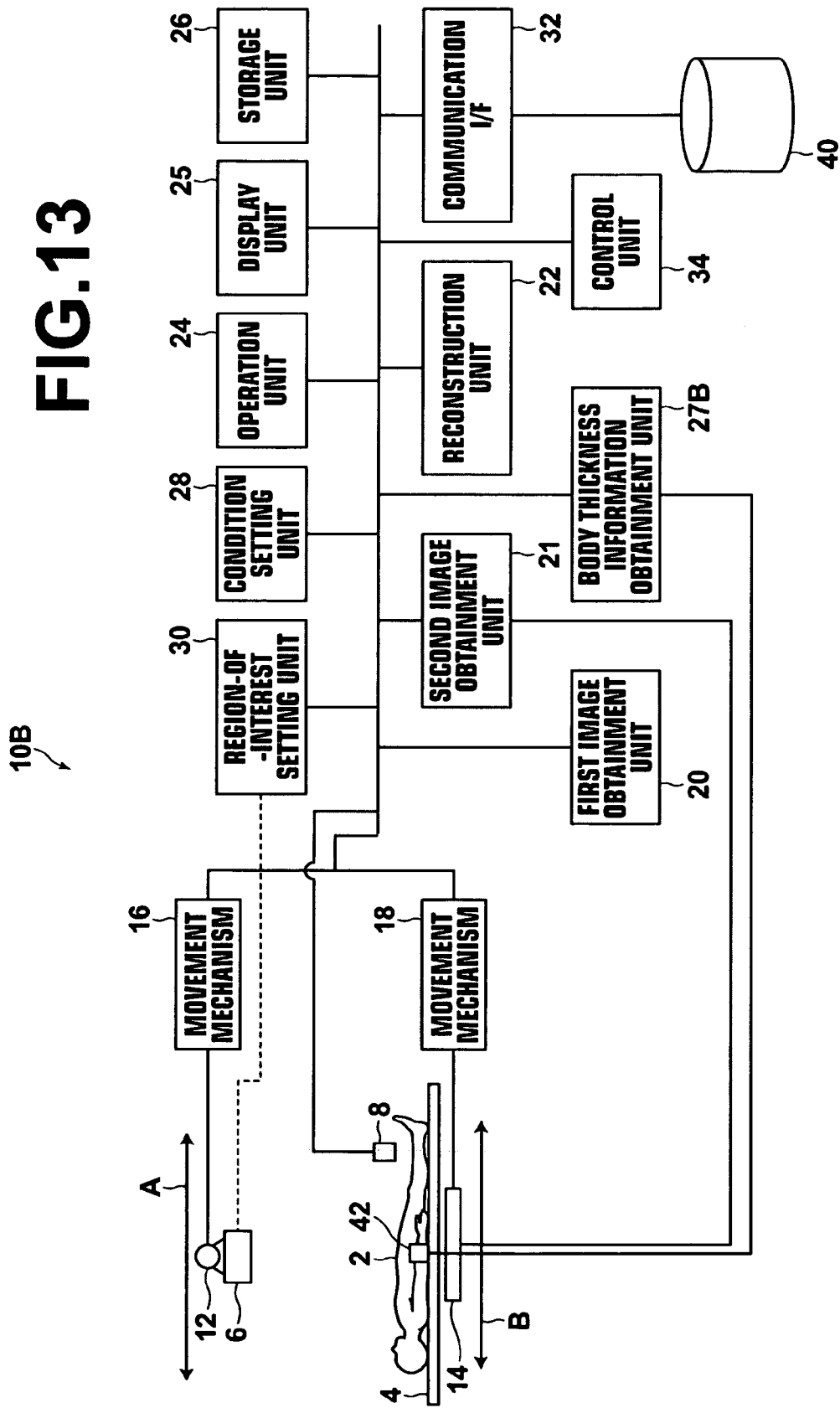
FIG. 13 is a schematic diagram illustrating the configuration of an X-ray radiography apparatus for performing tomosynthesis radiography to which a radiography apparatus according to a third embodiment of the present invention has been applied.

Next, a third embodiment of the present invention will be described. FIG. 13 is a schematic diagram illustrating the configuration of an X-ray radiography apparatus for performing tomosynthesis radiography to which a radiography apparatus according to the third embodiment of the present invention has been applied. In the third embodiment, the same reference numerals are assigned to the same elements as the elements of the first embodiment, and detailed descriptions of the elements are omitted. An X-ray radiography apparatus 10B of the third embodiment differs from the first embodiment in that the body thickness information about the subject 2 is obtained by a sensor 42, such as an infrared ray sensor and an ultrasonic sensor, which is arranged in the vicinity of the top board 4 of the radiographic table in the third embodiment. In the third embodiment, the condition setting unit 28 sets the slice image obtainment condition based on the body thickness information in a manner similar to the first embodiment.

Figure 14:
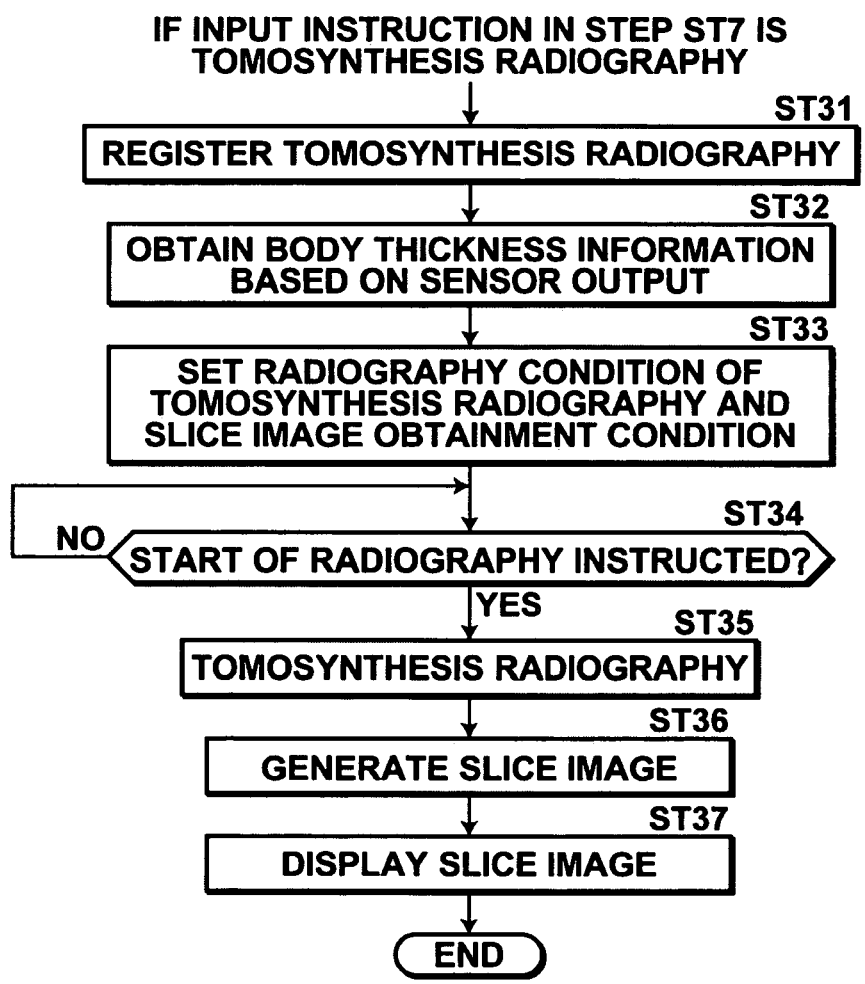
FIG. 14 is a flow chart showing process performed in the third embodiment of the present invention.

Next, the processing performed in the second third will be described. FIG. 14 is a flow chart illustrating the process performed in the third embodiment. In the third embodiment, only the process in step ST8 and thereafter differs from the process illustrated in the flow chart of FIG. 7 in the first embodiment. Therefore, only the process in step ST8 and thereafter will be described.

In the flow chart illustrated in FIG. 7, if the input in step ST7 is YES (tomosynthesis radiography), the control unit 34 registers, as diagnosis to be performed, tomosynthesis radiography (step ST31). Further, the body thickness information obtainment unit 27B obtains body thickness information about the subject 2 based on an output from the sensor 42 (step ST32). Further, the condition setting unit 28 sets the radiography condition of tomosynthesis radiography. Further, the condition setting unit 28 sets, based on the body thickness information, slice image obtainment condition. The slice image obtainment condition represents a range that is a target of generating a slice image in the subject 2 (step ST33). When the operator inputs a radiography start instruction (step ST34 is YES), the second image obtainment unit 21 performs tomosynthesis radiography, and obtains a plurality of radiographic images (step ST35). At this time, judgment is made as to whether the subject has moved by a distance exceeding a predetermined threshold value from the time of plain radiography to the time of tomosynthesis radiography. If the subject 2 has not moved by the distance exceeding the predetermined threshold value, radiography is not performed on the subject 2 at the predetermined radiation source position Sc. Further, the reconstruction unit 22 generates a slice image by reconstructing the slice image from the plurality of radiographic images so that the slice image in the range represented by the slice image obtainment condition is obtained (step ST36). The control unit 34 displays the slice image on the display unit 25 (step ST37), and processing ends. The generated slice image is stored in a storage device, such as a HDD, which is not illustrated. Alternatively, the generated slice image may be sent to a server 40 through a network.

As described above, the slice image obtainment condition is set based on the body thickness information also in the third embodiment. Therefore, it is possible to efficiently set the slice image obtainment condition based on the body thickness of the subject 2. Hence, it is possible to efficiently obtain the slice image.

In the third embodiment, the sensor, such as the ultrasonic sensor, is used. However, it is not necessary that the sensor is used. Any device or method may be adopted as long as a body thickness of the subject 2 is measured. For example, the body thickness information about the subject 2 may be obtained based on an image of the subject 2 imaged by using a camera or the like. In the first through third embodiments, only the X-ray tube 12 is moved. Needless to say, the present invention may be applied to a case in which both of the X-ray tube 12 and the detector 14 are moved in such a manner to be synchronized with each other.

In the first through third embodiments, tomosynthesis radiography is performed on a subject (patient) who is placed, in decubitus position, on a radiographic table. Needless to say, the present invention may be applied to tomosynthesis radiography using a radiographic table for standing position.

In the first through third embodiments, the radiography apparatus of the present invention is applied to an X-ray radiography apparatus that performs tomosynthesis radiography. Alternatively, the radiography apparatus of the present invention may be applied to a radiography apparatus (tomograph or tomography apparatus) that performs tomography. Next, a case of applying the radiography apparatus of the present invention to the tomography apparatus will be described as a fourth embodiment.

FIG. 15 is a schematic diagram illustrating the configuration of an X-ray radiography apparatus for performing tomography to which a radiography apparatus according to the fourth embodiment of the present invention has been applied. In the fourth embodiment, the same reference numerals are assigned to the same elements as the elements of the first embodiment, and detailed descriptions of the elements are omitted.

In the tomosynthesis radiography, a plurality of radiographic images are obtained by irradiating the subject 2 with X-rays at a plurality of radiation source positions in a discrete manner while the X-ray tube 12 is moved. Further, a slice image is generated by reconstructing the slice image from the plurality of radiographic images. In contrast, in tomography, which is performed by an X-ray radiography apparatus 10C of the fourth embodiment, the X-ray tube 12 and the detector 14 are relatively moved to opposite directions from each other in such a manner to be linked with each other. While the X-ray tube 12 and the detector 14 are moved, the subject 2 is continuously irradiated with X-rays a multiple times. Accordingly, the slice image generation unit 48 generates the slice image.

In tomography, a slice image is generated by one radiography operation. Therefore, when a plurality of slice images representing a plurality of slice planes are obtained in a desired range of slice planes, the manner of moving the X-ray tube 12 and the detector 14 at the time of radiography is changed, and radiography is performed a plurality of times. Therefore, in the fourth embodiment, the body thickness information obtainment unit 27C obtains body thickness information about the subject 2, and the condition setting unit 28 sets, based on the body thickness information, the desired range of slice images as the slice image obtainment condition. Further, tomography is performed in such a manner that a plurality of slice images are obtained in the range of slice images based on the set slice image obtainment condition.

In the fourth embodiment, body thickness information about the subject 2 may be obtained by using a pre-shot image in a manner similar to the first embodiment. Alternatively, a sensor may be used to obtain the body thickness information about the subject 2 in a manner similar to the third embodiment.

As described above, the slice image obtainment condition is set based on the body thickness information also in the fourth embodiment. Therefore, it is possible to efficiently set the slice image obtainment condition based on the body thickness of the subject 2. Hence, it is, possible to efficiently obtain the slice image also in the case of performing tomography.

What is claimed is:

1. A radiography apparatus comprising:
a radiation source that outputs radiation to a subject;
a detector that detects the radiation that has passed through the subject and produces an image of the subject;
a body thickness information obtainment unit that obtains body thickness information about the subject from the image of the subject;
a condition setting unit that sets, based on the body thickness information, a slice image obtainment condition representing a range in which a slice image is obtained in the subject; and
a slice image obtainment unit that obtains, based on the slice image obtainment condition, the slice image,
wherein the slice image obtainment unit obtains a plurality of radiographic images corresponding to a plurality of radiation source positions by moving the radiation source, relative to the detector, to the plurality of radiation source positions and by irradiating the subject with the radiation from the plurality of radiation source positions, and obtains the slice image of the subject by reconstructing the slice image from the plurality of radiographic images, and
wherein the body thickness information obtainment unit obtains the body thickness information about the subject by analyzing the plurality of radiographic images.

2. A radiography apparatus, as defined in claim 1, further comprising:
an image obtainment unit that obtains a pre-shot image by performing pre-shot radiography in which the radiation is output from the radiation source to the subject,
wherein the image of the subject is the pre-shot image, and
wherein the body thickness information obtainment unit obtains the body thickness information about the subject based on a distribution range of pixel values in the pre-shot image.

3. A radiography apparatus, as defined in claim 1, wherein the body thickness information obtainment unit reconstructs an orthogonal slice image from the plurality of radiographic images, the orthogonal slice image representing a slice plane orthogonal to the detector, and obtains the body thickness information about the subject based on an area in which the subject is present in the orthogonal slice image.

4. A radiography apparatus, as defined in claim 1, further comprising:
a storage unit that stores past radiography conditions about a plurality of subjects, wherein the condition setting unit refers to the past radiography conditions stored in the storage unit, and sets, based on the past radiography condition about the subject to be radiographed, the slice image obtainment condition if the past radiography condition about the subject to be radiographed is stored in the storage unit.

* * * * *